United States Patent
Tomaru

(10) Patent No.: US 7,403,292 B2
(45) Date of Patent: Jul. 22, 2008

(54) FLUID ANALYSIS ELEMENT AND FLUID ANALYSIS APPARATUS

(75) Inventor: Yuichi Tomaru, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 250 days.

(21) Appl. No.: 11/452,932

(22) Filed: Jun. 15, 2006

(65) Prior Publication Data

US 2006/0285115 A1 Dec. 21, 2006

(30) Foreign Application Priority Data

Jun. 15, 2005 (JP) ............................ 2005-174706
May 26, 2006 (JP) ............................ 2006-146444

(51) Int. Cl.
G01N 21/41 (2006.01)
G01N 21/00 (2006.01)

(52) U.S. Cl. ..................... 356/517; 356/436; 422/82.09

(58) Field of Classification Search ................. 356/517, 356/481, 436; 422/82.09
See application file for complete search history.

(56) References Cited

U.S. PATENT DOCUMENTS

2006/0281018 A1* 12/2006 Tomaru ........................ 430/5
2007/0008467 A1* 1/2007 Tomaru ....................... 349/114
2007/0263221 A1* 11/2007 Naya et al. ................... 356/432

FOREIGN PATENT DOCUMENTS

JP 2001-174719 A 6/2001
WO WO 2002/082042 A2 10/2002

* cited by examiner

Primary Examiner—Patrick J Connolly
(74) Attorney, Agent, or Firm—Sughrue Mion, PLLC

(57) ABSTRACT

A fluid analysis element includes: a semi transmissive/semi reflective first reflector; a transmissive apertured member, having a plurality of apertures, with diameters sufficiently smaller than the wavelength of measuring light, formed therein for holding a fluid sample; and a second reflector, which is fully reflective or semi transmissive/semi reflective. The first reflector, the transmissive apertured member, and the second reflector are provided in this order from the side of the element into which the measuring light enters. Emitted light is emitted from the first reflector or the second reflector. The element displays absorption properties that absorb light of specific wavelengths according to the mean complex refractive indices of the first and second reflectors, and the mean complex refractive index and the thickness of the transmissive apertured member. Analysis of the fluid sample is performed by detecting physical properties or changes in physical properties that occur according to the absorption properties.

16 Claims, 3 Drawing Sheets

FLUID ANALYSIS ELEMENT AND FLUID ANALYSIS APPARATUS

BACKGROUND OF THE INVENTION

1. Field of the Invention

The present invention relates to a novel fluid analysis element for analyzing the refractive indices, concentrations, and the like of fluid samples. The present invention also relates to a fluid analysis apparatus.

2. Description of the Related Art

Interference filters, such as etalon filters, are known as light modulating elements that absorb specific wavelengths of light and modulate the light. Conventional interference filters are difficult to manufacture, due to the high requirements regarding accuracy of smoothness and film thickness, and therefore are expensive. In addition, it is difficult to manufacture conventional interference filters having large areas, due to these reasons. Further, because the structures of the conventional interference filters are fixed, the light modulating properties thereof are also fixed. Accordingly, in the case that the wavelength of light to be absorbed (filtered) changes, a different interference filter needs to be provided, which precludes flexibility in design changes to optical systems.

In view of this, International Patent Publication No. WO2002/082042 discloses a light modulating element comprising an apertured member having fine apertures (nodes) with diameters of 1.0 to 1.6 µm, which are filled with fluids. This light modulating element is of a photonic crystal structure, in which the diameters of the fine apertures are greater than the wavelength of light. This light modulating element modulates light with the interference effects of photonic crystals.

Japanese Unexamined Patent Publication No. 2001-174719 discloses a light modulating element comprising a container, in which a pair of light transmissive wall members is provided. The wall members are separated in the direction of an optical axis, and the distance therebetween is adjustable. Fluid fills the space between the walls within the container. In this light modulating device, multiple reflection (resonance) occurs between the pair of transmissive wall members, to cause multiple beam interference. Thereby, light of specific wavelengths is absorbed, and the light is modulated.

The light modulating elements disclosed in International Patent Publication No. WO2002/082042 and Japanese Unexamined Patent Publication No. 2001-174719 both are capable of changing the light modulating properties by changing the fluid therein. However, it is difficult to perform fine high resolution light modulation as is possible with etalon filters.

SUMMARY OF THE INVENTION

In view of the foregoing circumstances, the present inventor researched light modulating elements, and invented a light modulating element which is capable of performing fine high resolution light modulation, changing light modulating properties, is easy to manufacture, and is capable of being manufactured having large areas. The present inventor further continued to research, and discovered that this light modulating element could be applied to analyze the refractive index and the concentration of fluid samples, and to identify fluid samples. Neither International Patent Publication No. WO2002/082042 nor Japanese Unexamined Patent Publication No. 2001-174719 disclose nor suggest application of the light modulating elements as fluid analysis elements.

Conventionally, the analysis of the refractive index and the concentration of fluid samples had been realized by measuring refractive angles by use of prisms and the like. The fluid analysis element invented by the present inventor does not measure the refractive angles of fluid samples, and is novel. That is, the present invention provides a novel fluid analysis element and a fluid analysis apparatus that employs the fluid analysis element.

The fluid analysis element of the present invention is to be employed to analyze fluid samples, in which a measuring light beam that enters the fluid analysis element is emitted as an emitted light beam having different physical properties depending on the type of fluid sample to be analyzed, and comprises:

a first reflector, which is semi transmissive/semi reflective;

a transmissive apertured member, having a plurality of fine apertures, with diameters smaller than the wavelength of the measuring light beam, formed therein for holding the fluid sample; and a second reflector, which is fully reflective or semi transmissive/semi reflective;

the first reflector, the transmissive apertured member, and the second reflector being provided in the order of enumeration from the side of the fluid analysis element into which the measuring light beam enters;

the emitted light beam being emitted from at least one of the first reflector and the second reflector;

the fluid analysis element displays absorption properties that absorb light of specific wavelengths according to the mean complex refractive index of the first reflector, the mean complex refractive index of the second reflector, and the mean complex refractive index and the thickness of the transmissive apertured member; and the analysis of the fluid sample is performed by detecting the physical properties or changes in physical properties that occur according to the absorption properties.

In the present specification, "semi transparent/semi reflective" means that a reflector has both transmissive and reflective qualities. The ratio of transmittance and reflectance can be set as desired. The phrase "diameters sufficiently smaller than the wavelength of the measuring light beam" defines the diameters of the fine apertures as being ½ or less than the shortest wavelength within a wavelength range of the measuring light beam. The "mean complex refractive index and the thickness of the transmissive apertured member" refers to the mean of the complex refractive index of the transmissive apertured member and the refractive index of the substance within the fine apertures (in the state that a fluid sample is held therein, the fluid sample, and in the state that no fluid sample is held therein, air). The "fluid sample" may be an unknown sample or a reference sample.

A configuration may be adopted, wherein:

the transmissive apertured member is formed by an oxidized metal member, obtained by anodizing a portion of a metallic member;

the second reflector is formed by a portion of the metallic member which has not been anodized; and the first reflector is formed by a metal film, which is coated on the transmissive apertured member.

A configuration may be adopted, wherein:

the transmissive apertured member is formed by an oxidized metal member, obtained by anodizing the entirety of a metal member; and the first reflector and the second reflector are respectively formed by metal films, which are coated on the transmissive apertured member.

A configuration may be adopted, wherein:

the transmissive apertured member is formed by an oxidized metal member, obtained by anodizing a portion of a metal member and then removing the non-anodized portion; and the first reflector and the second reflector are respectively formed by metal films, which are coated on the transmissive apertured member.

The fluid analysis element of the present invention is of a resonant structure, in which multiple reflection occurs effectively between the first reflector and the second reflector. Multiple beam interference occurs effectively due to the multiply reflected light beams, and strong absorption occurs with respect to light beams of specific wavelengths. The details of this phenomenon will be described later, but the absorbed wavelengths vary according to the refractive index of the fluid sample. Therefore, highly accurate analysis of the fluid sample is enabled, by detecting the physical properties or changes in physical properties that occur according to the absorption properties.

PCT Japanese Publication No. 2000-506267 discloses a fluid analysis element having a resonant structure, comprising an interference filter formed by porous silicon embedded in a silicon wafer, or embedded in a silicon layer formed on the silicon wafer. This fluid analysis element has a different resonant structure than that of the present invention, which comprises the first reflector, the transmissive apertured member, and the second reflector, provided in this order from the side of the element into which the measuring light beam enters. The resonant structure of the fluid analysis element of the present invention is easier to manufacture, and capable of being manufactured to have a large area. In addition, porous silicon is generally manufactured by processing silicon wafers with hydrofluoric acid. However, silicon wafers are costly, and the use of hydrofluoric acid, which contains halogen, is not preferable from an environmental standpoint. It has also been reported that porous silicon naturally oxidizes in high humidity environments, to generate silane gas (Adv. Mater. Vol. 6, pp. 865, 1994.)

The fluid analysis element of the present invention is easily manufactured by an anodizing process, and does not employ porous silicon. Therefore, the fluid analysis element of the present invention is superior to that disclosed in PCT Japanese Publication No. 2000-506267 from the viewpoints of ease of manufacture of the resonant structure, the ability to be manufactured with large areas, manufacturing costs, environmental considerations, and stability in storage.

However, porous silicon may be employed as the transmissive apertured member in the fluid analysis element of the present invention as well. Even in the case that porous silicon is employed as the transmissive apertured element, however, the fluid analysis element of the present invention has a different resonant structure from that of the fluid analysis element disclosed in PCT Japanese Publication No. 2000-506267, and is superior from the viewpoints of ease of manufacture and the ability to be manufactured with large areas.

Japanese Unexamined Patent Publication No. 5(1993)-051075 discloses a fluid analysis element, comprising an interference filter formed by a transmissive finely apertured member. In this element, a space between the apertured member (12) and a cover (17) is filled with fluid. A coherent light beam generated by interference between a light beam reflected at the upper surface of the apertured member (12) and a light beam reflected at an interface between the lower surface of the apertured member (12) and a metal substrate (11) is detected to perform analysis (refer to FIG. 1 of Publication No. 5-61075). This element differs from the fluid analysis element in terms of the element structure and the coherent light beam to be detected. The fluid analysis element of the present invention enables detection of multiple beam interference light, and thereby more highly accurate analysis is made possible.

A configuration may be adopted in the fluid analysis element of the present invention, wherein:

the transmissive apertured member comprises a plurality of analysis regions, at which a plurality of different fluid samples are held; and analysis of the different fluid samples is enabled at each of the plurality of analysis regions.

The fluid analysis apparatus of the present invention comprises:

the aforementioned fluid analysis element of the present invention;

measuring light emitting means, for irradiating a measuring light beam onto the fluid analysis element; and detecting means, for detecting the physical properties or changes in physical properties of an emitted light beam, which is emitted from the fluid analysis element.

In the fluid analysis apparatus of the present invention, it is preferable that:

the detecting means detects at least one of: the intensity of the emitted light beam; variation in the intensity of the emitted light beam; wavelengths of light which are absorbed by the fluid analysis element; and shifts in the wavelengths of light which are absorbed by the fluid analysis element.

The fluid analysis apparatus of the present invention is capable of analyzing at least one of the refractive index and the concentration of a fluid sample, and of analyzing the refractive index of a fluid sample to identify the fluid sample.

The fluid analysis element of the present invention comprises the semi reflective/semi transmissive first reflector, the transmissive apertured member having fine apertures formed therein with diameters sufficiently smaller than the wavelength of the measuring light beam, and the fully reflective or semi reflective/semi transmissive second reflector, provided in this order from the side of the element into which the measuring light beam enters.

In this structure, light beams that pass through the first reflector and enter the transmissive apertured member are repeatedly reflected between the first reflector and the second reflector, to effectively cause multiple reflection, which in turn effectively causes multiple beam interference. The multiple beam interference conditions vary according to the mean complex refractive index of the first reflector, the mean complex refractive index of the second reflector, and the mean complex refractive index and the thickness of the transmissive apertured member. Therefore, the fluid analysis element exhibits absorption properties that absorb light of specific wavelengths according to these factors. The mean complex refractive index of the transmissive apertured member varies according to the refractive index of the fluid sample. All of the factors other than the refractive index of the fluid sample are fixed. Therefore, the fluid sample can be analyzed, by detecting the physical properties or changes in physical properties that occur according to the absorption properties.

The fluid analysis apparatus of the present invention comprises the fluid analysis element of the present invention, the measuring light emitting means, and the detecting means. Therefore, analysis of fluid samples can be performed automatically by employing the fluid analysis element of the present invention. The fluid analysis apparatus of the present invention is capable of analyzing the refractive index and/or the concentration of the fluid sample, and is also capable of identifying the fluid sample, based on the refractive index thereof.

BEST MODE FOR CARRYING OUT THE INVENTION

First Embodiment

Figure 1A:
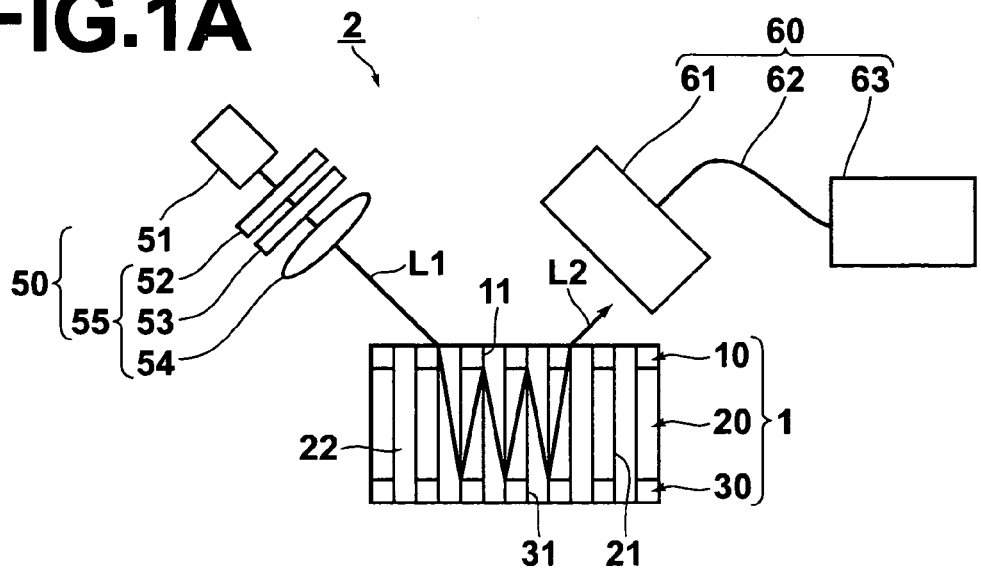
FIG. 1A is a schematic view of an entire fluid analysis apparatus according to a first embodiment.
Figure 1B:
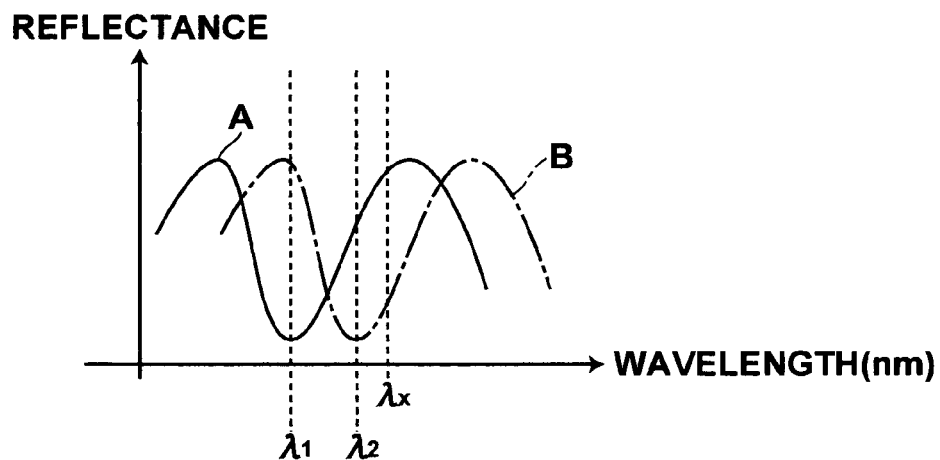
FIG. 1B is a graph illustrating examples of spectra of reflected light beams.
Figure 2A:
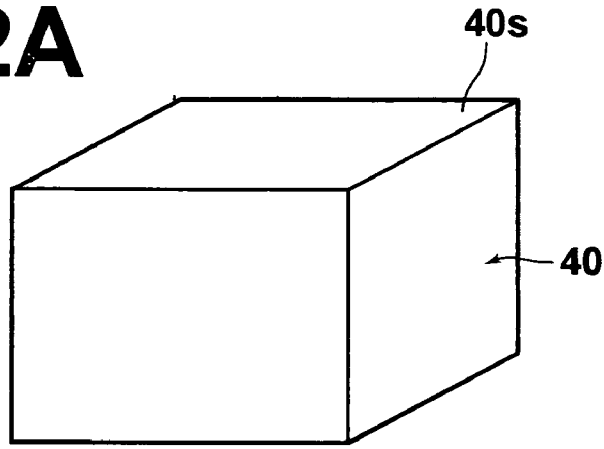
FIGS. 2A through 2C are perspective views that illustrate the manufacturing steps of the fluid analysis element 1.
Figure 2B:
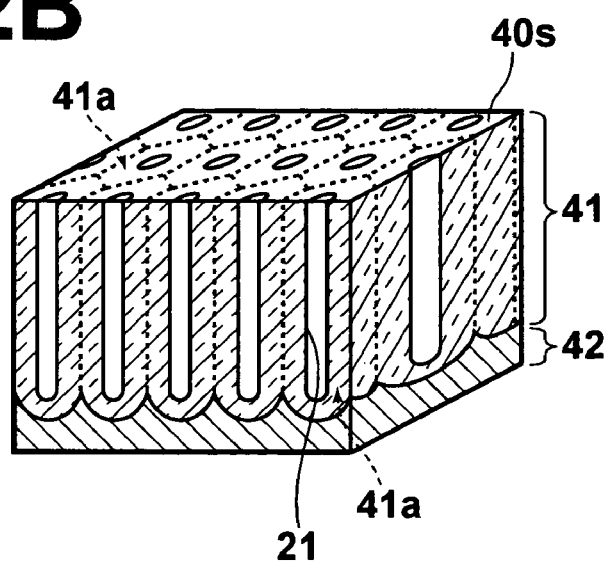
Figure 2C:
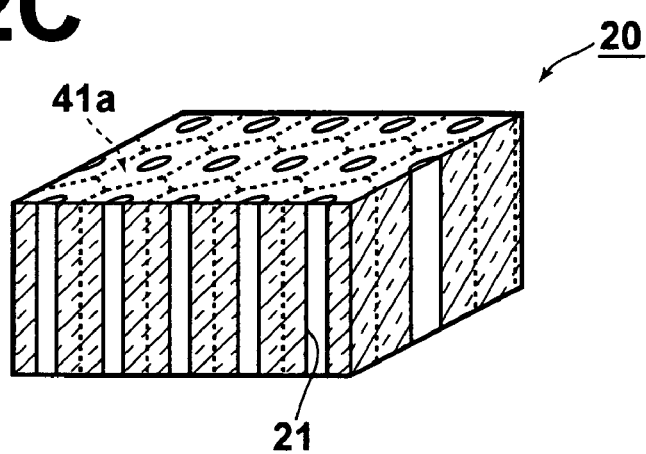

A fluid analysis element 1 according to a first embodiment of the present invention and a fluid analysis apparatus 2 that employs the fluid analysis element will be described with reference to FIGS. 1A through FIG. 2C. FIG. 1A is a schematic view of the entire fluid analysis apparatus 2 of the first embodiment (the fluid analysis element 1 is illustrated in cross section in the thickness direction thereof, with hatching omitted). FIG. 1B is a graph illustrating examples of spectra of reflected light beams. FIGS. 2A through 2C are perspective views that illustrate the manufacturing steps of the fluid analysis element 1.

As illustrated in FIG. 1A, the fluid analysis apparatus 2 comprises: the fluid analysis element 1 that emits an emitted light beam L2, which has different physical properties depending on the type of fluid sample 22, when a measuring light beam L1 enters thereinto; a measuring light emitting means 50, for irradiating the measuring light beam L1 onto the fluid analysis element 1; and a detecting means 60, for detecting the physical properties or the changes in physical properties of the emitted light L2.

The measuring light emitting means 50 comprises: a light source 51; and a light guiding optical system 55, for guiding the light emitted from the light source 51 to the fluid analysis element 1. Examples of the light source 51 include, but are not limited to: a single wavelength light source (such as a laser), and a white light source (such as a tungsten lamp). The light guiding optical system 55 is designed as appropriate, according to the type of light source adopted as the light source 51, and the physical properties or the changes in physical properties to be detected by the detecting means 60. For example, the light guiding optical system 55 may comprise: a collimating lens 52, for collimating the light emitted from the light source 51; a polarizing element 53, for restricting the emitted light to a specific polarization as necessary; and a focusing lens 54.

The detecting means 60 comprises, for example: a photoreceptor 61, for receiving the emitted light beam L2 emitted from the fluid analysis element 1; an optical fiber 62, for guiding the received light beam L2; and a detector 63, for detecting the physical properties or the changes in physical properties of the light beam L2 led thereto by the optical fiber 62.

The fluid analysis element 1 comprises: a semi transmissive/semi reflective first reflector 10; a transmissive apertured member 20; and a semi transmissive/semi reflective second reflector 30; provided in this order from the side of the element 1 into which the measuring light beam L1 enters (the upper side in FIG. 1A).

As illustrated in FIG. 1A and FIG. 2C, the transmissive apertured body 20 is formed by alumina ($Al_2O_3$, a light transmissive metal oxide), in which a plurality of substantially straight fine apertures 21 are formed such that they extend from the side of the first reflector 10 toward the second reflector 30. All of the plurality of fine apertures 21 penetrate through the transmissive apertured body 20, and are open at the surfaces thereof on the side of the first reflector 10 and on the side of the second reflector 30. The fine apertures 21 have diameters sufficiently smaller than the wavelength of the measuring light beam L1, and are provided at substantially regular pitches, which are also sufficiently smaller than the wavelength of the measuring light beam L1.

In the first embodiment, the fluid sample 22, which are the targets of analysis, fills the fine apertures 21. The fluid sample 22 may be an unknown sample, or a reference sample.

As illustrated in FIGS. 2A through 2C, the transmissive apertured member 20 is formed by: anodizing a portion of a metal member 40 having aluminum (Al) as its main component and impurities therein (preferably, the impurities are included as 10% or less); and then removing a non-anodized portion 42 and the vicinity thereof by etching.

The anodizing process may be performed by: immersing the metal member 40, as an anode, in an electrolytic solution along with a cathode; and applying a voltage between the anode and the cathode. The shape of the metal member 40 is preferably a plate shape, but is not limited thereto. The metal member 40 may alternatively be formed as a film layer on a substrate. Carbon, aluminum, or the like are used as the cathode. The acidic electrolytic solution may be, but is not limited to: sulfuric acid; phosphoric acid; chromium acid; oxalic acid; sulfamic acid; benzene sulfonic acid; amide sulfonic acid, and combinations of the above.

As illustrated in FIGS. 2B and 2C, when the metal member 40 is anodized, acidic reactions progress from the upper surface 40s in a direction substantially perpendicular thereto, and a metal oxide member 41 ($Al_2O_3O$) is generated. The metal oxide member 41 generated by the anodizing process is of a structure in which substantially hexagonal columns 41a are arranged without gaps therebetween. A fine aperture 21 that extends into the metal member 40 from the surface 40s is formed at the approximate center of each of the hexagonal columns 41a. The bottoms of the hexagonal columns 41a are rounded. The structure of the metal oxide member generated by the anodizing process is described in H. Masuda, "Preparation of Mesoporous Alumina by Anodization and Applications thereof as a Functional Material", Scientific Technology, Vol. 15, No. 10, pp. 34, 1997.

An example of favorable anodizing conditions for generating the metal oxide member 41, which is of a regularly arranged structure, in the case that oxalic acid is employed as the electrolytic solution, is: an electrolytic solution concentration of 0.5M; a solution temperature within the range of 14 to 16° C.; and an applied voltage of 40±0.5V. The fine apertures 21 which are generated under these conditions have diameters of 30 to 95 nm, and are arranged at pitches of approximately 100 nm, for example.

The transmissive apertured member 20 may alternatively be formed by anodizing the entirety of the metal member 40, without leaving the non-anodized portion 42.

The first reflector 10 and the second reflector 30 are both formed by metal films, which are formed on the transmissive apertured body 20 by a vapor deposition method or the like.

The fine apertures 21 penetrate through the transmissive apertured member 20 and are open on the surfaces thereof. Therefore, the metal films are not formed at the portions that correspond to the fine apertures 21, as illustrated in FIG. 1A. The first reflector 10 and the second reflector 30 respectively have apertures 11 and 31 that correspond to and communicate with the fine apertures 21 of the transmissive apertured member 20. The apertures 11 and 31 are provided in the same patterns as that of the fine apertures 21, and therefore have diameters which are sufficiently smaller than the wavelength of the measuring light beam L1, and are arranged substantially regularly at pitches which are also sufficiently smaller than the wavelength of the measuring light beam L1.

The first reflector 10 and the second reflector 30 maybe formed by the same material or by different materials. The materials of the first reflector 10 and the second reflector 30 are not limited, as long as they are metals that exhibit reflectivity. Examples are: Au; Ag; Cu; Al; alloys thereof; and combinations of two or more types of metals. The first reflector 10 and the second reflector 30 may also contain desired non-metallic components as impurities.

In the first embodiment, the fluid sample 22 can be introduced into and discharged from the fine apertures 21 of the transmissive apertured body 20 via the apertures 11 of the first reflector 10 and/or the apertures 31 of the second reflector 30. In the first embodiment, the fluid sample 22 may fill the apertures 11 and/or the apertures 31 in addition to the fine apertures 21. FIG. 1A illustrates an example in which the fluid sample 22 fills the apertures 11 and the apertures 31, that is, a state in which the transmissive apertured body 20 is filled to maximum capacity.

The fine apertures 21 of the transmissive apertured member 20 are provided with diameters and at pitches sufficiently smaller than the wavelength of the measuring light beam L1. Therefore, the transmissive apertured member 20 operates as a thin film with respect to light by the so-called electromagnetic mesh shield effect, both in an empty state prior to the fine apertures 21 being filled with the fluid sample 22, and in a full state after the fine apertures 21 are filled with the fluid sample 22.

Similarly, the apertures 11 and 31 of the first reflector 10 and the second reflector 30 are provided with diameters and at pitches sufficiently smaller than the wavelength of the measuring light beam L1. Therefore, the first reflector 10 and the second reflector 30 operate as thin films with respect to light, both in an empty state prior to the apertures 11 and 31 being filled with the fluid sample 22, and in a full state after the apertures 11 and 31 are filled with the fluid sample 22.

The first reflector 10 and the second reflector 30 are formed by reflective metals, but also have the apertures 11 and 31 formed therein. Therefore, the first reflector 10 and the second reflector 30 are semi transmissive and semi reflective. The transmissivity rate and the reflectivity of the first reflector 10 are determined by the material thereof, the thickness thereof, and the density at which the apertures 11 are provided. The transmissivity and the reflectance of the second reflector 10 are determined by the material thereof, the thickness thereof, and the density at which the apertures 31 are provided.

As illustrated in FIG. 1A, when the measuring light beam L1 is irradiated onto the fluid analysis element 1, a portion (not shown) of the measuring light beam L1 is reflected by the surface of the first reflector, and a portion passes through the first reflector 10 and enters the transmissive apertured member 20. The light that enters the transmissive apertured member 20 is repeatedly reflected between the first reflector 10 and the second reflector 30. That is, the fluid analysis element 1 has a resonant structure that causes multiple reflection to occur between the first reflector 10 and the second reflector 30.

Multiple beam interference occurs due to the multiple reflection within the fluid analysis element 1, and absorption properties that absorb light having specific wavelengths are exhibited. The multiple beam interference conditions vary according to the mean complex refractive index of the first reflector 10, the mean complex refractive index of the second reflector 30, and the mean complex refractive index and the thickness of the transmissive apertured member 20. Therefore, absorption properties that absorb light having specific wavelengths are exhibited according to these factors. The measuring light beam L1 is modulated according to the absorption properties, and emitted as the emitted light beam L2, which has different physical properties.

The mean complex refractive index of the first reflector 10 is designated as $n_1-ik_1$; the mean complex refractive index of the transmissive apertured member 20 is designated as $n_2$; the mean complex refractive index of the second reflector is designated as $n_3-ik_3$; and the thickness of the transmissive apertured member 20 is designated as d. In the first embodiment, $k_1$ and $k_3$ are extinction coefficients; $-ik_1$ and $-ik_3$ represent imaginary number portions; and the imaginary number portion of the mean complex refractive index of the transmissive apertured member 20 is 0.

The present inventor has discovered that in the case that the measuring light beam L1 enter the fluid analysis element 1 substantially perpendicularly, the peak wavelength λ of the light beam L1 (peak absorption wavelength λ), which is absorbed due to the multiple beat interference, depends largely on the mean complex refractive index $n_2$ and the thickness d of the transmissive apertured member 20, and has a relationship as defined in the following formulas. That is, the present inventor has discovered that the peak absorption wavelength λ appears in the vicinity of the wavelength represented by the formulas below, and changes according to the mean complex refractive index $n_1-ik_1$ of the first reflector 10, the mean complex refractive index $n_3-ik_3$ of the second reflector 30, and the mean complex refractive index $n_2$ and the thickness d of the transmissive apertured member 20, in the vicinity of the wavelength represented by the formulas below.

$$n_2 d \approx (m+1)/2\lambda$$

$$\lambda \approx (m+1) 2 n_2 d$$

wherein m is an arbitrary integer (0, ±1, ±2 ...)

Particularly in the case that at least one of the first reflector 10, the transmissive apertured member 20, and the second reflector 30 is constituted by a light absorbing member of which imaginary number portion of the complex dielectric constant is not 0, the absorption peak becomes sharp. That is, strong absorption properties are displayed for light having a specific wavelength. In the first embodiment, the first reflector 10 and the second reflector 30, which are metal films, function as light absorbing members.

It is preferable that the fluid analysis element 1 is of an optical impedance matched structure that maximizes the number of multiple reflections (finesse F) within the transmissive apertured member 20. Finesse F is generally represented by the following formula. The greater the reflectivity of the reflectors, the greater the finesse F becomes, and the sharper the absorption peak becomes.

$$\text{Finesse } F = \Pi R^{1/2}/(1-R)$$

The mean complex refractive index of the transmissive apertured member 20 varies according to the refractive index of the fluid sample 22. All of the factors other than the refractive index of the fluid sample 22 are fixed. Therefore, the fluid sample 22 can be analyzed, by detecting the physical properties or changes in physical properties of the emitted light beam L2 that occur according to the absorption properties with the detecting means 60.

In the first embodiment, both the first reflector 10 and the second reflector 30 are semi transmissive/semi reflective. Therefore, the fluid analysis element 1 becomes one of: a reflective element, in which the emitted light beam L2 is emitted from the first reflector 10; a transmissive element, in which the emitted light beam L2 is emitted from the second reflector 30; and a semi transmissive/semi reflective element, in which the emitted light beam L2 is emitted from both the first reflector 10 and the second reflector 30; depending on the mean complex refractive index $n_1-ik_1$ of the first reflector 10, the mean complex refractive index $n_3-ik_3$ of the second reflector 30, and the mean complex refractive index $n_2$ and the thickness d of the transmissive apertured member 20. The fluid analysis element 1 maybe selected to be the reflective element, the transmissive element, or the semi transmissive/semi reflective element as necessary. FIG. 1A illustrates the fluid analysis element 1 as a reflective element.

The thickness d of the transmissive apertured member 20 is not limited to a specific thickness. However, it is preferable that the thickness d is set to be 300 nm or less, because in this case, only one peak absorption wavelength occurs within the visible light wavelength spectrum.

FIG. 1B is a graph that illustrates an example of the change in spectrum of reflected light, in the case that the fluid analysis element 1 is a reflective element, the measuring light beam L1 is white light, and fluid samples A and B are introduced as the fluid sample 22. FIG. 1B illustrates the manner in which the peak absorption wavelength $\lambda$ changes from $\lambda_1$ to $\lambda_2$ by changing the type of fluid sample 22.

The mean complex refractive index $n_2$ of the transmissive apertured layer 20 is derived both when the fluid analysis element 1 is filled with the fluid sample A and the fluid sample B, based on the peak absorption wavelengths $\lambda_1$ and $\lambda_2$. The mean complex refractive index $n_2$ of the transmissive apertured member 20 is represented by the formula below. The percentage of the mean complex refractive index of the transmissive apertured member 20 made up by the refractive index of the fluid sample 22 is fixed. Therefore, the refractive indices of the fluid sample A and the fluid sample B can be derived, based on the peak absorption wavelengths $\lambda_1$ and $\lambda_2$. In the formula below, $n_p$ is the refractive index of the transmissive apertured member 20 (the portion formed by $Al_2O_3$); $n_x$ is the refractive index of the fluid sample 22; a is the volume fraction of the transmissive apertured member 20 (the portion formed by $Al_2O_3$); and b is the volume fraction of the fluid sample 22.

$$N_2 = an_p + bn_x$$

If the fluid sample A is a reference sample, of which the refractive index is known, the refractive index of the fluid sample B can be derived based on the shift in peak absorption wavelength $\Delta\lambda = \lambda_2 - \lambda_1$. The change $\Delta n_2$ in the mean refractive index of the transmissive apertured member 20 can be derived from the change $\Delta\lambda$ in peak absorption wavelength. The percentage of the change in refractive index of the fluid sample 22 that makes up the change in the mean refractive index of the transmissive apertured member 20 is fixed. Accordingly, if the refractive index of the reference sample A is designated as $n_0$, the refractive index $n_x$ of the unknown sample B can be derived by the following formula.

$$n_x = n_0 - (\Delta n_2/b)$$

In the case that the measuring light emitting means 50 comprises an optical system that irradiates broad spectrum light that includes the peak absorption wavelength $\lambda$, such as white light, the detector 63 may be a spectroscope or the like for detecting the peak absorption wavelength $\lambda$ or the shift $\Delta\lambda$ thereof. Then, the refractive index of the fluid sample 22 can be analyzed.

The measuring light emitting means 50 may alternatively comprise an optical system that irradiates a single wavelength light beam. In this case, the detector 63 may comprise photodiodes or the like, which are capable of detecting the intensity of light. If an arbitrary wavelength $\lambda_x$ within the spectrum illustrated in the graph of FIG. 1B is focused on, different reflective intensities are exhibited by the fluid samples A and B. Accordingly, the refractive index of the fluid sample 22 can be derived, by emitting light of the arbitrary wavelength $\lambda_x$ as the measuring light beam L1 and detecting the intensity of the emitted light beam L2 with the detector 63. The refractive index of the fluid sample B can also be derived in the case that the refractive index of the fluid sample A is known, by detecting the change in intensity of the emitted light beam L2.

That is, the detecting means 60 preferably detects at least one of: the intensity of the emitted light beam L2; the change in intensity of the emitted light beam L2; the wavelength of light which is absorbed by the fluid analysis element 1; and the shift in the wavelength absorbed by the fluid analysis element 1. The refractive index of the fluid sample 22 can be favorably analyzed by the fluid analysis apparatus 2 being equipped with such detecting means 60.

In the case that a plurality of fluid samples 22 having the same components at different concentrations, the refractive indices thereof change according to the concentration. Therefore, the concentrations of fluid samples 22 can also be derived from the refractive indices thereof. In the case that a plurality of fluid samples 22, which are the same except for the presence/absence of a specific substance, the refractive indices thereof change according to the presence/absence of the specific substance. Therefore, the presence/absence of the specific substance can be analyzed based on the refractive indices of the fluid samples 22. In addition, it is possible to identify a fluid sample 22 based on the refractive index thereof.

The fluid analysis element 1 and the fluid analysis apparatus 2 of the first embodiment is configured as described above.

The fluid analysis element 1 of the first embodiment comprises: the semi reflective/semi transmissive first reflector 10; the transmissive apertured member 20 having the fine apertures 21 for holding the fluid sample 22 formed therein with diameters sufficiently smaller than the wavelength of the measuring light beam; and the semi reflective/semi transmissive second reflector 30, provided in this order from the side of the element 1 into which the measuring light beam L1 enters.

In this structure, light beams that pass through the first reflector 10 and enter the transmissive apertured member 20 are repeatedly reflected between the first reflector 10 and the second reflector 30, to effectively cause multiple reflection, which in turn effectively causes multiple beam interference. The multiple beam interference conditions vary according to the mean complex refractive index of the first reflector 10, the mean complex refractive index of the second reflector 30, and the mean complex refractive index and the thickness of the transmissive apertured member 20. Therefore, the fluid analysis element 1 exhibits absorption properties that absorb light of specific wavelengths according to these factors. The mean complex refractive index of the transmissive apertured member 20 varies according to the refractive index of the fluid sample 22. All of the factors other than the refractive index of the fluid sample 22 are fixed. Therefore, the fluid sample 22 can be analyzed, by detecting the physical properties or changes in physical properties that occur according to the absorption properties. For example, the fluid sample 22 can be analyzed, by detecting at least one of: the intensity of the emitted light beam L2; the change in intensity of the emitted light beam L2; the wavelength of light which is absorbed by the fluid analysis element 1; and the shift in the wavelength absorbed by the fluid analysis element 1.

The fluid analysis apparatus 2 of the first embodiment comprises the fluid analysis element 1 of the present invention, the measuring light emitting means 50, and the detecting means 60. Therefore, analyses of fluid samples 22 can be performed automatically by employing the fluid analysis apparatus 2. The fluid analysis apparatus 2 is capable of analyzing the refractive index and/or the concentration of the fluid sample 22, and is also capable of identifying the fluid sample 22, based on the refractive index thereof.

The fluid analysis element 1 may adopt a configuration, in which the transmissive apertured member 20 comprises a plurality of analysis regions, at which a plurality of different fluid samples 22 are held; and analyses of the different fluid samples 22 are enabled at each of the plurality of analysis regions. In this case, the detecting means 60 may be configured to detect the physical properties or changes in physical properties of the emitted light L2 separately for each of the analysis regions. For example, the fluid analysis apparatus 2 may comprise a photoreceptor 61 constituted by a plurality of light receiving elements that correspond in number and arrangement pattern to the analysis regions of the fluid analysis element. In this case, the detector 63 may perform detection with respect to the emitted light beam L2 received by each of the light receiving elements. In the fluid analysis apparatus 2 of this construction, analyses of a plurality of fluid samples 22 can be performed simultaneously. Therefore, this fluid analysis apparatus 2 maybe favorably applied to biological analysis, in which a plurality of samples having the same basic components except for a specific condition are simultaneously analyzed.

The fluid analysis element 1 of the first embodiment has a structure which is sufficiently smaller than the wavelength of the measuring light beam L1 as a minimum unit of light modulation. Therefore, the fluid analysis element 1 exhibits fine high resolution light modulating properties, and is capable of performing highly accurate analysis. In addition, the fluid analysis element 1 of the first embodiment comprises the transmissive apertured member 20, in which the plurality of fine apertures 21 are arranged regularly. Therefore, the planar uniformity of the light modulating properties is high. Accordingly, stable fluid analysis can be performed, even in the case that analyses of fluid samples 22 are performed with respect to a plurality of analysis regions.

Note that in the first embodiment, it is not necessary for the number of reflections that occur within the transmissive apertured member 20 to be high. The number of reflections may be arbitrary, as long as multiple beam interference occurs effectively, fine high resolution light modulation is possible, and accurate analysis can be performed.

The fluid analysis element 1 of the first embodiment has a structure in which the transmissive apertured member 20 is sandwiched between the first reflector 10 and the second reflector 30. By utilizing the anodizing process, manufacture of the fluid analysis element 1 is facilitated, as is manufacture of fluid analysis elements 1 having large areas.

The fluid analysis element 1 of the first embodiment possesses wavelength selectivity based on its structure. Therefore, deterioration (such as discoloration) of the element is unlikely to occur, which provides superior stability of use over long periods of time.

Second Embodiment

Figure 3:
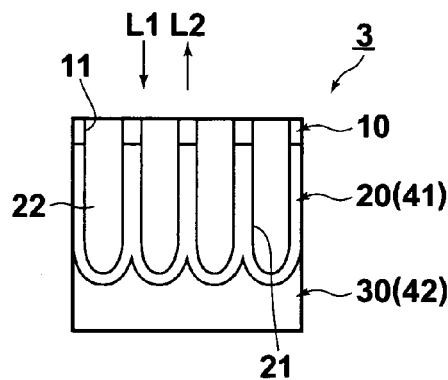
FIG. 3 is a diagram that illustrates the construction of a fluid analysis element according to a second embodiment of the present invention.

Next, a fluid analysis element 3 according to a second embodiment of the present invention will be described with reference to FIG. 3. The basic structure of the fluid analysis element 3 is the same as that of the fluid analysis element 1 of the first embodiment. Therefore, common structural elements are denoted with the same reference numerals, and detailed descriptions thereof will be omitted. FIG. 3 corresponds to the illustration of the fluid analysis element 1 of FIG. 1A.

The fluid analysis element 3 of the second embodiment comprises: a first reflector 10; a transmissive apertured member 20; and a second reflector 30; provided in this order from the side of the element 3 into which the measuring light beam L1 enters, similar to the fluid analysis element 1. However the fluid analysis element 3 differs from the fluid analysis element 1 in that fine apertures 21 of the transmissive apertured member 20 do not penetrate therethrough, and that the second reflector 30 is completely reflective. The fine apertures 21 of the transmissive apertured member 20 are only open at the side toward the first reflector 10, and are closed at the side toward the second reflector 30.

The transmissive apertured member 20 is formed by the anodized metal oxide 41 ($Al_2O_3$) illustrated in FIG. 2B, and second reflector 30 is formed by the non-anodized portion 42 (Al) illustrated in FIG. 2B. The first reflector 10 is formed by a metal film, which is formed on the transmissive apertured member 20.

In the fluid analysis element 3 as well, light that passes through the first reflector 10 and enters the transmissive apertured member 20 is repeatedly reflected between the first reflector 10 and the second reflector 30, to effectively cause multiple reflection. The multiple reflection effectively causes multiple beam interference to occur. The multiple beam interference conditions vary according to the mean complex refractive index of the first reflector 10, the mean complex refractive index of the second reflector 30, and the mean complex refractive index and the thickness of the transmissive apertured member 20. Therefore, absorption properties that absorb light having specific wavelengths are exhibited according to these factors. The mean complex refractive index of the transmissive apertured member 20 varies according to the refractive index of the fluid sample 22. All of the factors other than the refractive index of the fluid sample 22 are fixed. Therefore, the fluid sample 22 can be analyzed, by detecting the physical properties or changes in physical properties of that occur according to the absorption properties.

In the second embodiment, the second reflector 30 is completely reflective. Therefore, the fluid analysis element 3 of the second embodiment can only be a reflective element, in which an emitted light beam L2 is emitted from the first reflector 10.

In the second embodiment as well, it is preferable that a fluid sample 22 is analyzed by detecting at least one of: the intensity of the emitted light beam L2; the change in intensity of the emitted light beam L2; the wavelength of light which is absorbed by the fluid analysis element 3; and the shift in the wavelength absorbed by the fluid analysis element 3. The fluid analysis element 3 of the second embodiment is capable of analyzing the refractive index and/or the concentration of fluid samples 22 similarly to the fluid analysis element 1 of the first embodiment. It is also possible to identify fluid samples 22 based on the refractive indices thereof.

The fluid analysis element 3 may also adopt a configuration, in which the transmissive apertured member 20 comprises a plurality of analysis regions, at which a plurality of different fluid samples 22 are held; and analyses of the different fluid samples 22 is enabled at each of the plurality of analysis regions. In this case, simultaneous analyses of a plurality of fluid samples 22 are enabled.

The fluid analysis element 3 of the second embodiment has a structure which is sufficiently smaller than the wavelength of the measuring light beam L1 as a minimum unit of light modulation. Therefore, the fluid analysis element 3 exhibits fine high resolution light modulating properties, and is capable of performing highly accurate analysis. In addition, the fluid analysis element 3 of the second embodiment comprises the transmissive apertured member 20, in which the plurality of fine apertures 21 are arranged regularly. Therefore, the planar uniformity of the light modulating properties is high. Accordingly, stable fluid analysis can be performed, even in the case that analyses of fluid samples 22 are performed with respect to a plurality of analysis regions.

The fluid analysis element 3 of the second embodiment has a structure in which the transmissive apertured member 20 is sandwiched between the first reflector 10 and the second reflector 30. Manufacture of the fluid analysis element 3 is facilitated by the anodizing process, and manufacture of the fluid analysis element 3 having a large area is also easy.

The fluid analysis element 3 of the second embodiment possesses wavelength selectivity based on its structure. Therefore, deterioration (such as discoloration) of the element is unlikely to occur, which provides superior stability of use over long periods of time.

Similarly to the first embodiment, a fluid analysis apparatus may be configured by combining the fluid analysis element 3 with a measuring light emitting means 50 and a detecting means 60, to enable automatic analyses of fluid samples 22.

(Design Modifications)

The present invention is not limited to the aforementioned embodiments. Various modifications may be made to the design, as long as they do not stray from the spirit of the present invention.

In the first and second embodiments, the main component of the metal member 40, which is anodized to form the transmissive apertured member, was Al. However, any desired metal can be utilized, as long as the metal oxide thereof generated by anodization exhibits light transmissive qualities. Examples of such metals include: Ti, Ta, Hf, Zr, Si, In, and Zn. The metal member 40 to be anodized may be a combination of two or more types of metals.

By utilizing the anodizing process, manufacture of the transmissive apertured member 20 having the regularly arranged fine apertures 21 is facilitated, as is manufacture of fluid analysis elements having large areas. The manufacture of the transmissive apertured member 20 having superior structural regularity is facilitated. Therefore, the planar uniformity of the light modulating properties is high. Accordingly, manufacture of fluid analysis elements capable of stable fluid analysis, even in the case that analyses of fluid samples 22 are performed with respect to a plurality of analysis regions, is facilitated.

It is preferable to utilize the anodizing process as described above. However, the present invention is not limited to utilizing the anodizing process, and the fluid analysis element may be manufactured by utilizing other techniques for forming fine apertures. Examples of such techniques include: electron beam printing methods, in which fine apertures (including penetrative apertures and non-penetrative recesses) are drawn on a transmissive substrate by a Focused Ion Beam (FIB) or an Electron Beam (EB); and lithography methods, in which a transmissive apertured member constituted by a desired uneven pattern is formed on a completely reflective or a semi transmissive/semi reflective substrate (in this case, the recesses of the uneven pattern function as the fine apertures). By using methods other than the anodizing process, the variety of materials for the transmissive apertured members, the degree of freedom in design of the pattern of the fine apertures 21, and the like are increased.

The materials of the first reflector 10 and the second reflector 30 are not limited to metals, and may be any material that exhibits reflectivity.

The shapes of the fine apertures may also be set as desired. In the embodiments described above, the fine apertures were substantially straight circular columns. Alternatively, the fine apertures may be triangular columns, rectangular columns, and the like. As a further alternative, the shapes of the fine apertures 21 may be random. The fine apertures are also not limited to being columnar.

The arrangement pattern of the fine apertures 21 may also be set as desired. The plurality of fine apertures 21 may be arranged one dimensionally or two dimensionally in the first reflector 10 in directions parallel to the surface into which the measuring light beam L1 enters. The embodiments described above are examples in which the fine apertures 21 are arranged two dimensionally in the first reflector 10 in directions parallel to the surface into which the measuring light beam L2 enters. Alternatively, the fine apertures 21 may be arranged three dimensionally, in which the fine apertures 21 are also arranged in the thickness direction of the transmissive apertured member 20. As a further alternative, the arrangement of the fine apertures 21 may be random.

As described in the "Summary of the Invention" section of the specification, the fluid analysis element of the present invention comprises the resonant structure that causes multiple beam interference to occur effectively. Therefore, highly accurate analysis is enabled. In addition, the fluid analysis element of the present invention is easily manufactured by an anodizing process, and does not employ porous silicon. Accordingly, the fluid analysis element of the present invention is superior in the ease of manufacture of the resonant structure, the ease of being manufactured to have large areas, manufacturing costs, environmental considerations, stability in storage, and accuracy of analysis.

[Implementation]

Examples of implementation of the present invention will be described.

<Manufacture of the Fluid Analysis Element>

The reflective fluid analysis element 3 according to the second embodiment of the present invention was manufactured in the following manner. The transmissive apertured member 20 was formed by anodizing a portion of a metal member 40 having Al as its main component. The transmissive apertured member 20 ($Al_2O_3$) had a thickness d of 250 nm, and an aperture ratio (total area of the openings of the fine apertures/total area of the transmisive apertured member 20) of ½. The second reflector 30 was formed by the non-anodized portion (Al) of the metal member 40. The first reflector 10 was formed as a gold film, formed by vapor deposition on the surface of the transmissive apertured member 20.

The complex refractive index of a substance varies according to the wavelength of light incident thereon. The complex refractive indices of Au, $Al_{2O3}$, and Au; the mean complex refractive index of the first reflector 10; the mean complex refractive index of the transmissive apertured member 20 in a state in which the fine apertures are empty (filled with air, which has a refractive index n=1); and the mean complex refractive index of the second reflector 30 are listed below for reference. The mean complex refractive index of the first reflector 10 is calculated while taking the aperture ratio of the fine apertures 21 into consideration. The second reflector 30 has no apertures formed therein. Therefore, the mean complex refractive index of the second reflector 30 is the same as the complex refractive index of Al.

Complex Refractive Indices:

| Au | $0.175-i3.10$ |
|---|---|
| $Al_2O_3$ | 1.767 |
| Al | $0.97-i6.00$ |

Mean Complex Refractive Indices:

| First Reflector 10 ($n_1-ik_1$) | $0.725-i3.10$ |
|---|---|
| Empty Transmissive Apertured Member 20 ($n_2$) | 1.256 |
| Second Reflector 30 ($n_3-ik_3$) | $0.97-i6.00$ |

<Evaluation>

The spectrum of light reflected by the fluid analysis element 3 when white light (emitted by a xenon lamp) was irradiated thereon in an empty state (Condition 1) was measured employing a "Polychrometer M25" (Bunko Instruments). The "empty state" refers to a state in which there are no fluid samples 22 in the fine apertures 21, and the fine apertures 21 are filled with air having a refractive index n=1. The reflected light intensity was normalized by the spectrum of light reflected by alumina, which was obtained in advance.

The plurality of fine apertures 21 were filled with different types of fluid samples 22, and similar evaluations were performed. The first type of fluid sample 22 was water (refractive index n=1.33, Condition 2). The second type of fluid sample 22 was 100% ethanol (refractive index n=1.36, Condition 3).

The mean complex refractive index of the transmissive apertured member 20 under each of the above three conditions are listed below.

Condition 1: 1.256

Condition 2: 1.476

Condition 3: 1.496

<Results>

Figure 4:
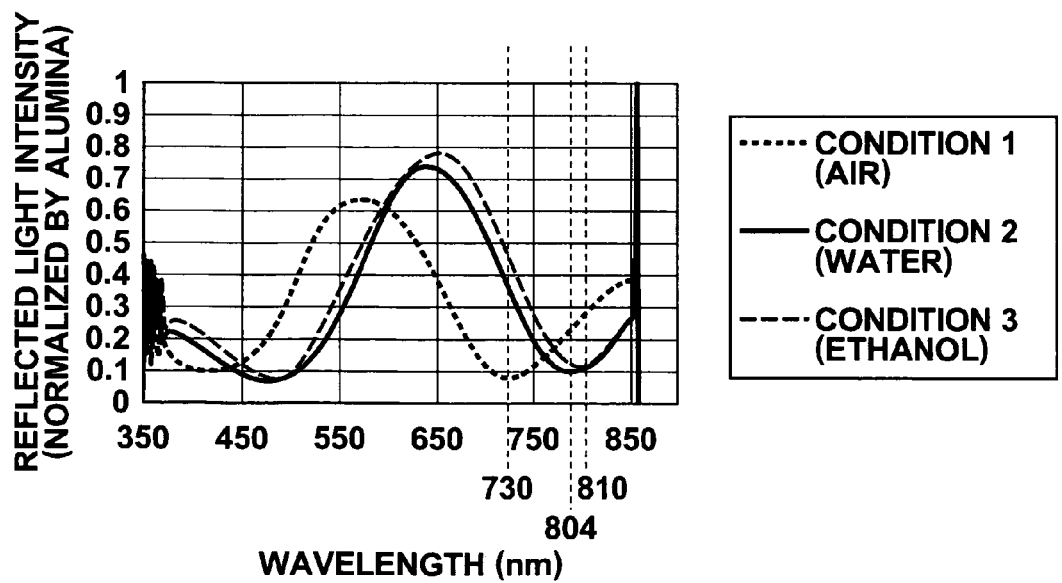
FIG. 4 is a graph that illustrates the evaluation results of an embodiment of the present invention.

The obtained spectra of reflected light are illustrated in FIG. 4. As illustrated in FIG. 4, absorption peaks due to multiple beam interference can be observed in each of Condition 1, in which the fine apertures 21 were empty (filled with air), Condition 2, in which the fine apertures 21 were filled with water, and Condition 3, in which the fine apertures 21 were filled with ethanol. The obtained reflected light spectra exhibit different peak absorption wavelengths under each of the conditions. The peak absorption wavelengths $\lambda$ were: 730 nm under Condition 1; 804 nm under Condition 2; and 810 nm under Condition 3.

From the forgoing, it was shown that the fluid analysis element 3 exhibits different absorption properties according to the type of fluid sample 22 filled therein, and is capable of analyzing fluid samples 22 based on the peak absorption wavelength $\lambda$, shifts therein, and the like.

The fluid analysis element and the fluid analysis apparatus of the present invention can be utilized to analyze and identify fluid samples, by analyzing the refractive indices and/or concentrations thereof.

What is claimed is:

1. A fluid analysis element, to be employed to analyze fluid samples, in which a measuring light beam that enters the fluid analysis element is emitted as an emitted light beam having different physical properties depending on the type of fluid sample to be analyzed, comprising:
   a first reflector, which is semi transmissive/semi reflective;
   a transmissive apertured member, having a plurality of fine apertures, with diameters sufficiently smaller than the wavelength of the measuring light beam, formed therein for holding the fluid sample; and
   a second reflector, which is fully reflective or semi transmissive/semi reflective;
   the first reflector, the transmissive apertured member, and the second reflector being provided in the order of enumeration from the side of the fluid analysis element into which the measuring light beam enters;
   the emitted light beam being emitted from at least one of the first reflector and the second reflector;
   the fluid analysis element displaying absorption properties that absorb light of specific wavelengths according to the mean complex refractive index of the first reflector, the mean complex refractive index of the second reflector, and the mean complex refractive index and the thickness of the transmissive apertured member; and
   the analysis of the fluid sample being performed by detecting the physical properties or changes in physical properties that occur according to the absorption properties.

2. A fluid analysis element as defined in claim 1, wherein:
   the fine apertures are open at the side of the transmissive apertured member toward the first reflector;
   a plurality of apertures corresponding to the fine apertures of the transmissive apertured member are formed through the first reflector; and
   the fluid sample is introduced to and discharged from the fine apertures through the apertures of the first reflector.

3. A fluid analysis element as defined in claim 1, wherein:
   the fine apertures are open at the side of the transmissive apertured member toward the second reflector;
   a plurality of apertures corresponding to the fine apertures of the transmissive apertured member are formed through the second reflector; and
   the fluid sample is introduced to and discharged from the fine apertures through the apertures of the second reflector.

4. A fluid analysis element as defined in claim 2, wherein:
   the fine apertures are substantially straight apertures that extend from the side of the transmissive apertured member toward the first reflector toward the side of the transmissive apertured member toward the second reflector.

5. A fluid analysis element as defined in claim 3, wherein:
   the fine apertures are substantially straight apertures that extend from the side of the transmissive apertured member toward the first reflector toward the side of the transmissive apertured member toward the second reflector.

6. A fluid analysis element as defined in claim 2, wherein:
   the transmissive apertured member is formed by an oxidized metal member, obtained by anodizing a portion of a metallic member;
   the second reflector is formed by a portion of the metallic member which has not been anodized; and
   the first reflector is formed by a metal film, which is coated on the transmissive apertured member.

7. A fluid analysis element as defined in claim 3, wherein:
the transmissive apertured member is formed by an oxidized metal member, obtained by anodizing a portion of a metallic member;
the second reflector is formed by a portion of the metallic member which has not been anodized; and
the first reflector is formed by a metal film, which is coated on the transmissive apertured member.

8. A fluid analysis element as defined in claim 2, wherein:
the transmissive apertured member is formed by an oxidized metal member, obtained by anodizing the entirety of a metal member; and
the first reflector and the second reflector are respectively formed by metal films, which are coated on the transmissive apertured member.

9. A fluid analysis element as defined in claim 2, wherein:
the transmissive apertured member is formed by an oxidized metal member, obtained by anodizing a portion of a metal member and then removing the non-anodized portion; and
the first reflector and the second reflector are respectively formed by metal films, which are coated on the transmissive apertured member.

10. A fluid analysis element as defined in claim 3, wherein:
the transmissive apertured member is formed by an oxidized metal member, obtained by anodizing the entirety of a metal member; and
the first reflector and the second reflector are respectively formed by metal films, which are coated on the transmissive apertured member.

11. A fluid analysis element as defined in claim 3, wherein:
the transmissive apertured member is formed by an oxidized metal member, obtained by anodizing a portion of a metal member and then removing the non-anodized portion; and
the first reflector and the second reflector are respectively formed by metal films, which are coated on the transmissive apertured member.

12. A fluid analysis element as defined in claim 1, wherein:
the transmissive apertured member comprises a plurality of analysis regions, at which a plurality of different fluid samples are held; and
analysis of the different fluid samples is enabled at each of the plurality of analysis regions.

13. A fluid analysis apparatus, comprising:
a fluid analysis element as defined in claim 1;
measuring light emitting means, for irradiating a measuring light beam onto the fluid analysis element; and
detecting means, for detecting the physical properties or changes in physical properties of an emitted light beam, which is emitted from the fluid analysis element.

14. A fluid analysis apparatus as defined in claim 13, wherein:
the detecting means detects at least one of: the intensity of the emitted light beam; variation in the intensity of the emitted light beam; wavelengths of light which are absorbed by the fluid analysis element; and shifts in the wavelengths of light which are absorbed by the fluid analysis element.

15. A fluid analysis apparatus as defined in claim 13, wherein:
at least one of the refractive index and the concentration of a fluid sample is analyzed.

16. A fluid analysis apparatus as defined in claim 13, wherein:
the refractive index of a fluid sample is analyzed to identify the fluid sample.

* * * * *